(12) United States Patent
Kleemann et al.

(10) Patent No.: US 6,451,781 B1
(45) Date of Patent: Sep. 17, 2002

(54) SUBSTITUTED ACYLGUANIDINES, PROCESS FOR THEIR PREPARATION, THEIR USE AS MEDICAMENTS OR DIAGNOSTICS, AND MEDICAMENTS COMPRISING THEM

(75) Inventors: Heinz-Werner Kleemann, Bischofsheim; Armin Hofmeister, Nierstein; Eugen Falk, Frankfurt; Hans-Willi Jansen, Niedernhausen; Hans-Ludwig Schäfer, Hochheim, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/655,725

(22) Filed: Sep. 5, 2000

(30) Foreign Application Priority Data

Sep. 2, 1999 (DE) .......................... 199 41 764

(51) Int. Cl.[7] .............. A61K 31/56; C07J 9/00; C07J 41/00
(52) U.S. Cl. .............. 514/182; 514/171; 514/182; 552/553; 552/554
(58) Field of Search ............. 514/182, 171; 552/553, 554

(56) References Cited

U.S. PATENT DOCUMENTS 5,610,151 A  3/1997  Glombik et al. ............ 514/172

6,166,002 A * 12/2000  Weichert et al. ............ 514/182

FOREIGN PATENT DOCUMENTS

| EP | 0 624 594 | 11/1994 |
|---|---|---|
| WO | WO 00/24761 | 5/2000 |

OTHER PUBLICATIONS

Derwent Abstract of WO 00/24761.

* cited by examiner

*Primary Examiner*—Sabiha Qazi
(74) *Attorney, Agent, or Firm*—Finnegan, Henderson, Farabow, Garrett & Dunner, LLP

(57) ABSTRACT

Substituted acylguanidines and their pharmaceutically tolerable salts and physiologically functional derivatives.

Compounds of the formula I

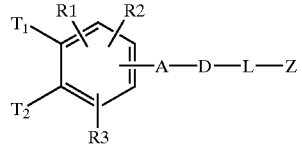

in which the radicals have the meanings indicated, and their physiologically tolerable salts, physiologically functional derivatives and a process for their preparation are described. The compounds are suitable, for example, as medicaments for the prophylaxis or treatment of gallstones.

9 Claims, No Drawings

SUBSTITUTED ACYLGUANIDINES, PROCESS FOR THEIR PREPARATION, THEIR USE AS MEDICAMENTS OR DIAGNOSTICS, AND MEDICAMENTS COMPRISING THEM

This application claims the benefit of foreign priority under 35 U.S.C. §119 to German patent application no. 19941764.4-43, filed on Sep. 2, 1999, the contents of which are incorporated by reference herein.

The invention relates to substituted acylguanidines and their pharmaceutically tolerable salts and physiologically functional derivatives.

In addition to a number of factors, the formation of gallstones is essentially determined by the composition of the bile, in particular by the concentration and the ratio of cholesterol, phospholipids and bile salts. A prerequisite for the formation of cholesterol gallstones is the presence of bile which is supersaturated in cholesterol (ref. Carey, M. C. and Small, D. M. (1978) The physical chemistry of cholesterol solubility in bile. Relationship to gallstone formation and dissolution in man, J. Clin. Invest. 61: 998–1026).

Up to now, gallstones have mainly been removed surgically, so that there is a great therapeutic need for the medicinal dissolution of gallstones and for the prevention of gallstone formation.

The invention was based on the object of making available compounds which are able to prevent the formation of gallstones by preventing the supersaturation of the bile with cholesterol, or by delaying the formation of cholesterol crystals from supersaturated biles.

The invention therefore relates to compounds of the formula I

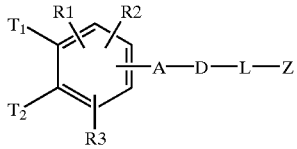

in which:
T1 and T2 independently of one another are

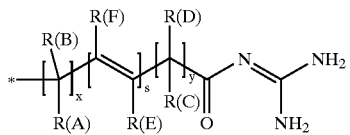

or hydrogen, where
T1 and T2 cannot simultaneously be hydrogen;
Z is

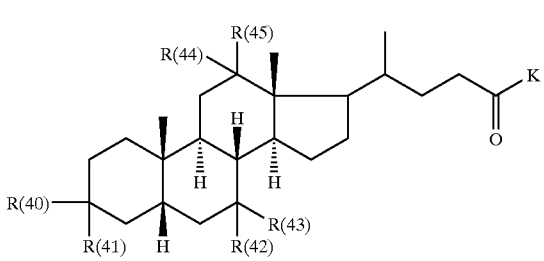

A is a bond, $(C_1-C_4)$-alkyl, $(C_0-C_4)$-alkyl-X;
X is —O—, —CO—, —CH[OH]—, —CH[OCH$_3$]—, —SO$_{(0-2)}$— or —NH—,—N(CH$_3$)—;
D is phenylene which is not substituted or is substituted by 1–3 substituents selected from the group consisting of F, Cl, —CF$_3$, $(C_1-C_4)$-alkyl, hydroxyl, methoxy, —NH$_2$, NHCH$_3$, N(CH$_3$)$_2$, CH$_3$SO$_2$— and H$_2$NO$_2$S—;

R(A), R(B), R(C), R(D), R(E), R(F) independently of one another are hydrogen, F, Cl, Br, I, CN, OH, OR(6), NR(7)R(8), $(C_1-C_8)$-alkyl, O—$(C_1-C_{12})$-alkyl, $(C_3-C_8)$-cycloalkyl, it being possible in the alkyl radicals for one, a number or all hydrogens to be replaced by fluorine;

R(6) is $(C_3-C_6)$-alkenyl, $(C_3-C_8)$-cycloalkyl, phenyl or benzyl, it being possible for the phenyl nucleus to be up to trisubstituted by F, Cl, CF$_3$, methyl, methoxy, NR(9)R(10);

R(9), R(10) independently of one another are H, $(C_1-C_4)$-alkyl or $(C_1-C_4)$-perfluoroalkyl;

R(7) and R(8) independently of one another are $(C_1-C_4)$-alkyl, $(C_3-C_6)$-alkenyl, $(C_3-C_8)$-cycloalkyl, phenyl or benzyl, it being possible for the phenyl nucleus to be up to trisubstituted by F, Cl, CF$_3$, methyl, methoxy, NR(9)R(10); or R(7) and R(8) together form a chain of 4 or 5 methylene groups, of which one CH$_2$ group can be replaced by oxygen, sulfur, NH, N—CH$_3$ or N-benzyl;

s is zero or 1,
x is zero, 1 or 2;
y is zero, 1 or 2;

R(1), R(2), R(3) independently of one another are hydrogen, F, Cl, Br, I, CN, —(C=O)—N=C(NH$_2$)$_2$, —SO$_{(0-1)}$—$(C_1-C_8)$-alkyl, O—$(C_0-C_4)$—alkylphenyl, —$(C_0-C_4)$-alkylphenyl, it being possible for the phenyl nucleus to be up to trisubstituted by F, Cl, CF$_3$, methyl, methoxy, —$(C_0-C_4)$-alkyl-NR(21)R(22);
$(C_1-C_8)$-alkyl, O—$(C_1-C_{12})$-alkyl, $(C_3-C_8)$-cycloalkyl, it being possible in the alkyl radicals for one, a number or all hydrogens to be replaced by fluorine;

R(21), R(22) independently of one another are H, $(C_1-C_4)$-alkyl;

L is $(C_1-C_{15})$-alkyl, it being possible for one or more (CH$_2$) groups to be replaced by —CH=CH—, —C≡C—, —O—, —NR(47)—, —NR(48)—, —CO—, —SO$_2$—;

R(47) is hydrogen, $(C_1-C_8)$-alkyl, R(48)—CO—, phenyl, benzyl;

R(48) is hydrogen, $(C_1-C_8)$-alkyl, phenyl, (CH$_2$)-phenyl, it being possible for the phenyl nucleus to be up to trisubstituted by F, Cl, CF$_3$, methyl, methoxy;

R(40) to R(45) independently of one another are H, —O R(50), —S R(50), NH R(50), —N R(50)$_2$, —O—(CO)— R(50), —S—(CO)— R(50), —NH—(CO)—R(50), —O—PO—(O R(50))—O R(50), —O—(SO$_2$)—O R(50), —R(50), a bond to L; or R(40) and R(41), R(42) and R(43), R(44) and R(45) in each case together are the oxygen of a carbonyl group; just one of the radicals always having the meaning of a bond to L;

R(50) is hydrogen, $(C_1-C_4)$-alkyl, phenyl, (CH$_2$)-phenyl, it being possible for the phenyl nucleus to be up to trisubstituted by F, Cl, CF$_3$, methyl, methoxy;

K is —OR(51), —NH(R51), —N(R51)$_2$, —HN—CH$_2$—CH$_2$—CO$_2$H, —HN—CH$_2$—CH$_2$—SO$_3$H, —N(CH$_3$) CH$_2$CO$_2$H, —HN—CH(R46)CO$_2$H, —OKa, Ka being a cation, such as, for example, an alkali metal or alkaline earth metal ion or a quaternary ammonium ion;

R(46) is hydrogen, C$_1$-C$_4$-alkyl, benzyl, —CH$_2$—OH, H$_3$CSCH$_2$CH$_2$—, HO$_2$CCH$_2$—, HO$_2$CCH$_2$CH$_2$—;

R(51) is H, $(C_1-C_4)$-alkyl, phenyl, (CH$_2$)-phenyl, it being possible for the phenyl radical to be up to trisubstituted by F, Cl, CF$_3$, methyl, methoxy;

and their pharmaceutically tolerable salts and physiologically functional derivatives.

Preferred compounds are those of the formula I

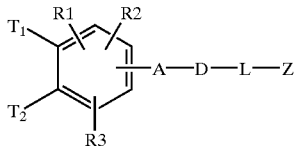

in which one or more radical(s) has or have the following meaning:

T1 and T2 independently of one another are equal to

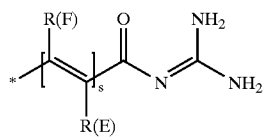

or hydrogen, where
T1 and T2 cannot simultaneously be hydrogen,
L—Z is

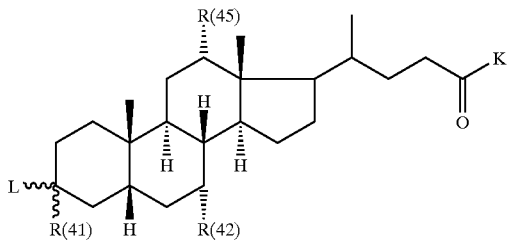

A is a bond, —CH$_2$—, CH$_2$—X—;
X is —O—, —CO—, —CH[OH]—, —CH[OCH$_3$]—, —SO$_{(0-2)}$— or —NH—, N(CH$_3$)—;
s is zero or 1;
D is phenylene which can be up to disubstituted by F, Cl, —CF$_3$, (C$_1$–C$_4$)-alkyl, hydroxyl, methoxy, —NH$_2$, NHCH$_3$, N(CH$_3$)$_2$, CH$_3$SO$_2$—, H$_2$NO$_2$S—;
R(E) is F, Cl, CN, OR(12), (C$_1$–C$_4$)-alkyl, O—(C$_1$–C$_4$)-alkyl, (C$_3$–C$_6$)-cycloalkyl, it being possible in the alkyl radicals for one, a number or all hydrogens to be replaced by fluorine;
R(6) is (C$_3$–C$_6$)-alkenyl, (C$_3$–C$_8$)-cycloalkyl, phenyl or benzyl, it being possible for the phenyl nucleus to be up to trisubstituted by F, Cl, CF$_3$, methyl, methoxy, NR(9) R(10);
R(9), R(10) independently of one another are H, (C$_1$–C$_4$)-alkyl or (C$_1$–C$_4$)-perfluoroalkyl;
R(F) is hydrogen;
R(1), R(2), R(3) independently of one another are hydrogen, F, Cl, Br, I, CN, —(C=O)—N=C(NH$_2$)$_2$, —SO$_{(0-1)}$—(C$_1$–C$_8$)-alkyl, O—(C$_0$–C$_4$)-alkylphenyl, —(C$_0$–C$_4$)-alkylphenyl, it being possible for the phenyl nucleus to be up to trisubstitued by F, Cl, CF$_3$, methyl, methoxy;
L is (C$_1$–C$_8$)-alkyl, where one or more (CH$_2$) groups can be replaced by —CH=CH—, —C≡C—, —O—, —NR(47)—, —NR(48)—, —CO—, —SO2—;
R(47) is hydrogen, (C$_1$–C$_4$)-alkyl, R(48)—CO—, phenyl, (CH$_2$)-phenyl;

R(47) is hydrogen, (C$_1$–C$_4$)-alkyl, R(48)-CO—, phenyl, (CH$_2$)-phenyl;
R(48) is hydrogen, (C$_1$–C$_4$)-alkyl, phenyl, (CH$_2$)-phenyl, it being possible methyl, methoxy;
R(41), R(42), R(45) independently of one another are H, —O R(50), —S R(50), NH R(50), —N R(50)$_2$, —O—(CO)— R(50), —S—(CO)— R(50), —NH—(CO)—R(50), —O—PO—(O R(50))—O R(50), —O—(SO$_2$)—O R(50), —R(50);
R(50) is hydrogen, (C$_1$–C$_4$)-alkyl, phenyl, (CH$_2$)-phenyl, it being possible for the phenyl nucleus to be up to trisubstitued by; F, Cl, CF$_3$, methyl, methoxy;
K is —OR(51), —NH(R51), —N(R51)$_2$, —HN—CH$_2$—CH$_2$—CO$_2$H, —HN—CH$_2$—CH$_2$—SO$_3$H, —N(CH$_3$) CH$_2$CO$_2$H, —HN—CH(R46)CO$_2$H, —OKa, Ka being a cation, such as, for example, an alkali metal or an alkaline earth metal ion or a quaternary ammonium ion,
R(46) is H, C$_1$–C$_4$-alkyl, benzyl, —CH$_2$—OH, H$_3$CSCH$_2$CH$_2$—, HO$_2$CCH$_2$—, HO$_2$CCH$_2$CH$_2$—;
R(51) is H, (C$_1$–C$_4$)-alkyl, phenyl, (CH$_2$)-phenyl, it being possible for the phenyl radical to be up to trisubstituted by F, Cl, CF$_3$, methyl, methoxy;

and their pharmaceutically tolerable salts.

Particularly preferred compounds are those of the formula I

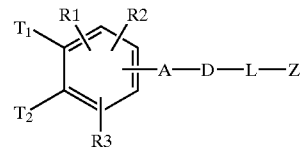

in which one or more radical(s) has or have the following meaning:

T1 and T2 independently of one another are equal to

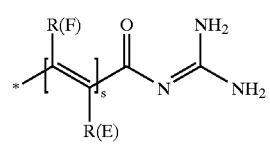

or hydrogen, where
T1 and T2 cannot simultaneously be hydrogen,
L—Z is

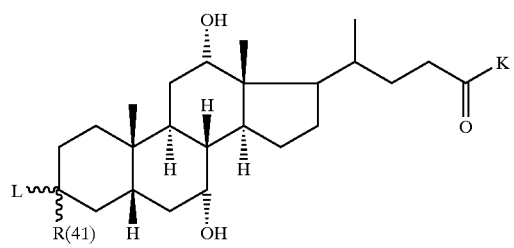

A is a bond, —CH$_2$—, CH$_2$—X—, —X—;
X is —O—, —CO—, —SO$_{(0-2)}$—;
s is zero or 1;
D is phenylene which can be up to disubstituted by F, Cl, —CF$_3$, (C$_1$–C$_4$)-alkyl, hydroxyl, methoxy, —NH$_2$, NHCH$_3$, N(CH$_3$)$_2$, CH$_3$SO$_2$—, H$_2$NO$_2$S;

R(E) is F, $(C_1-C_4)$-alkyl, it being possible in the alkyl radical for one, a number or all hydrogens to be replaced by fluorine;

R(F) is hydrogen;

R(1), R(2), R(3) independently of one another are hydrogen, F, Cl, CN, —$SO_2$—$CH_3$, O—$(C_0-C_1)$-alkylphenyl, —$(C_0-C_1)$-alkylphenyl, it being possible for the phenyl nucleus to be up to trisubstituted by F, Cl, $CF_3$, methyl, methoxy;

L is $(C_1-C_8)$-alkyl, it being possible for one or more ($CH_2$) groups to be replaced by —CH=CH—, —C≡C—, —O—, —NR(47)—, —NR(48)—, —CO—, —$SO_2$—;

R(47) is hydrogen, $(C_1-C_4)$-alkyl, R(48)—CO—, phenyl, ($CH_2$)-phenyl;

R(48) is hydrogen, $(C_1-C_4)$-alkyl, phenyl, ($CH_2$)-phenyl, it being possible for the phenyl nucleus to be up to trisubstituted by F, Cl, $CF_3$, methyl, methoxy;

R(41) is hydrogen, —OH;

K is —OR(51), —NH(R51), —N(R51)$_2$, —HN—$CH_2$—$CO_2H$, —HN—$CH_2$—$CH_2$—$CO_2H$, —HN—$CH_2$—$CH_2$—$SO_3H$, —N($CH_3$)$CH_2CO_2H$, —OKa, Ka being a cation, such as, for example, an alkali metal or alkaline earth metal ion or a quaternary ammonium ion;

R(51) is H, $(C_1-C_4)$-alkyl, phenyl, ($CH_2$)-phenyl, it being possible for the phenyl radical to be up to trisubstituted by F, Cl, $CF_3$, methyl, methoxy;

and their pharmaceutically tolerable salts.

Very particularly preferred compounds are those of the formula I

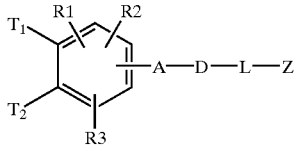

I in which one or more radical(s) has or have the following meaning:

T1 and T2 independently of one another are

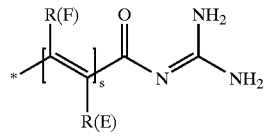

or hydrogen, where

T1 and T2 cannot simultaneously be hydrogen,

L—Z is

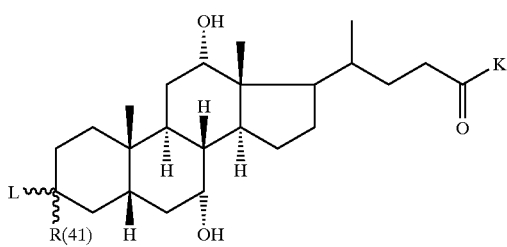

A is a bond, —O—;
s is zero or 1;

D is phenylene which can be up to disubstituted by F, Cl, —$CF_3$, $(C_1-C_4)$-alkyl, hydroxyl, methoxy, N($CH_3$)$_2$, $CH_3SO_2$—, $H_2NO_2S$;

R(E) is $(C_1-C_4)$-alkyl;

R(F) is hydrogen;

R(1), R(2), R(3) independently of one another are hydrogen, F, Cl, CN, —$SO_2$—$CH_3$, O—$(C_0-C_1)$-alkylphenyl, —$(C_0-C_1)$-alkylphenyl, it being possible for the phenyl nucleus to be up to trisubstituted by F, Cl, $CF_3$, methyl, methoxy;

L is $(C_1-C_6)$-alkyl, it being possible for one or more ($CH_2$) groups to be replaced by —CH=CH—, —C≡C—, —O—, —NR(47)—, —CO—, —$SO_2$—;

R(47) is hydrogen, $(C_1-C_4)$-alkyl;

R(41) is hydrogen, —OH;

K is —OH, —HN—$CH_2$—$CO_2H$, —HN—$CH_2$—$CH_2$—$CO_2H$, —HN—$CH_2$—$CH_2$—$SO_3H$, —N($CH_3$)$CH_2CO_2H$, —OKa, Ka being a cation, such as, for example, an alkali metal or alkaline earth metal ion or a quaternary ammonium ion;

and their pharmaceutically tolerable salts.

If the compound of the formula I contains one or more asymmetric centers, these can have either the S or R configuration. The compounds can be present as optical isomers, as diastereomers, as racemates or as mixtures thereof.

The double bond geometry of the compounds of the formula I can be either E or Z. The compounds can be present in the mixture as double bond isomers.

The designated alkyl radicals can be either straight-chain or branched.

The invention furthermore relates to a process for the preparation of the compound I (L—Z=acetylene-bile acid derivative), which comprises reacting a compound of the formula II,

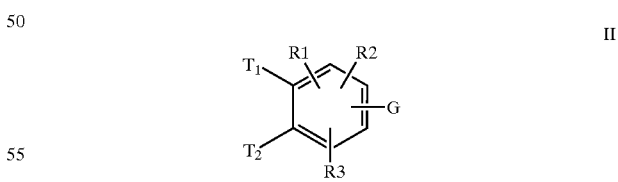

II in which T1, T2, R(1), R(2) and R(3) have the meaning indicated above and G is a functionality which can be replaced by L—Z, in a manner known to the person skilled in the art with a compound L—Z of the formula III. The functionality G of the compound having the formula II can have, for example, the meaning of bromine or iodine, as the desired C—C bond linkage is achieved by Pd(0) catalysis in the manner known to the person skilled in the art.

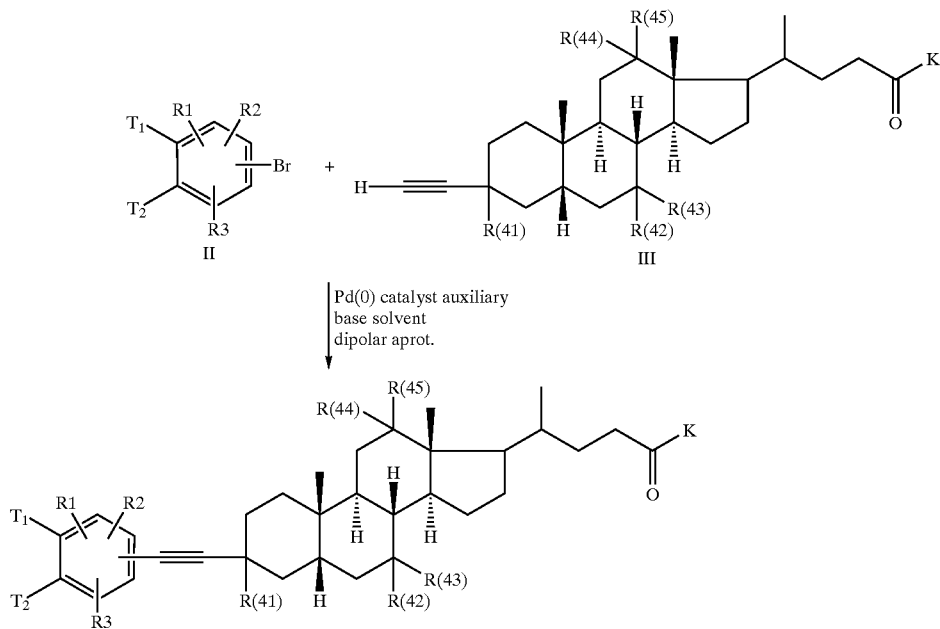

The acetylene-bile acid derivatives of the formula III are prepared from suitable bile acid ketones IV according to Scheme 1. These in turn can be prepared from bile acids V according to processes known from the literature or acquired commercially. To this end, lithiumacetylide is added to ketobile acids of type IV analogously to known processes (U.S. Pat. No. 5,641,767). The acetylene-bile acid derivatives III a thus obtained are deprotected, depending on the type of the protective groups used, in a one-pot process, e.g. with $X_3$, $X_4$=Oacyl, or in two steps, e.g. with $X_3$, $X_4$=THP, to give compounds III b. The carboxylic acid function of b can be converted into suitable esters such as, for example, benzyl, p-methoxybenzyl, trimethylsilyl or t-butylesters of type III c according to different known processes.

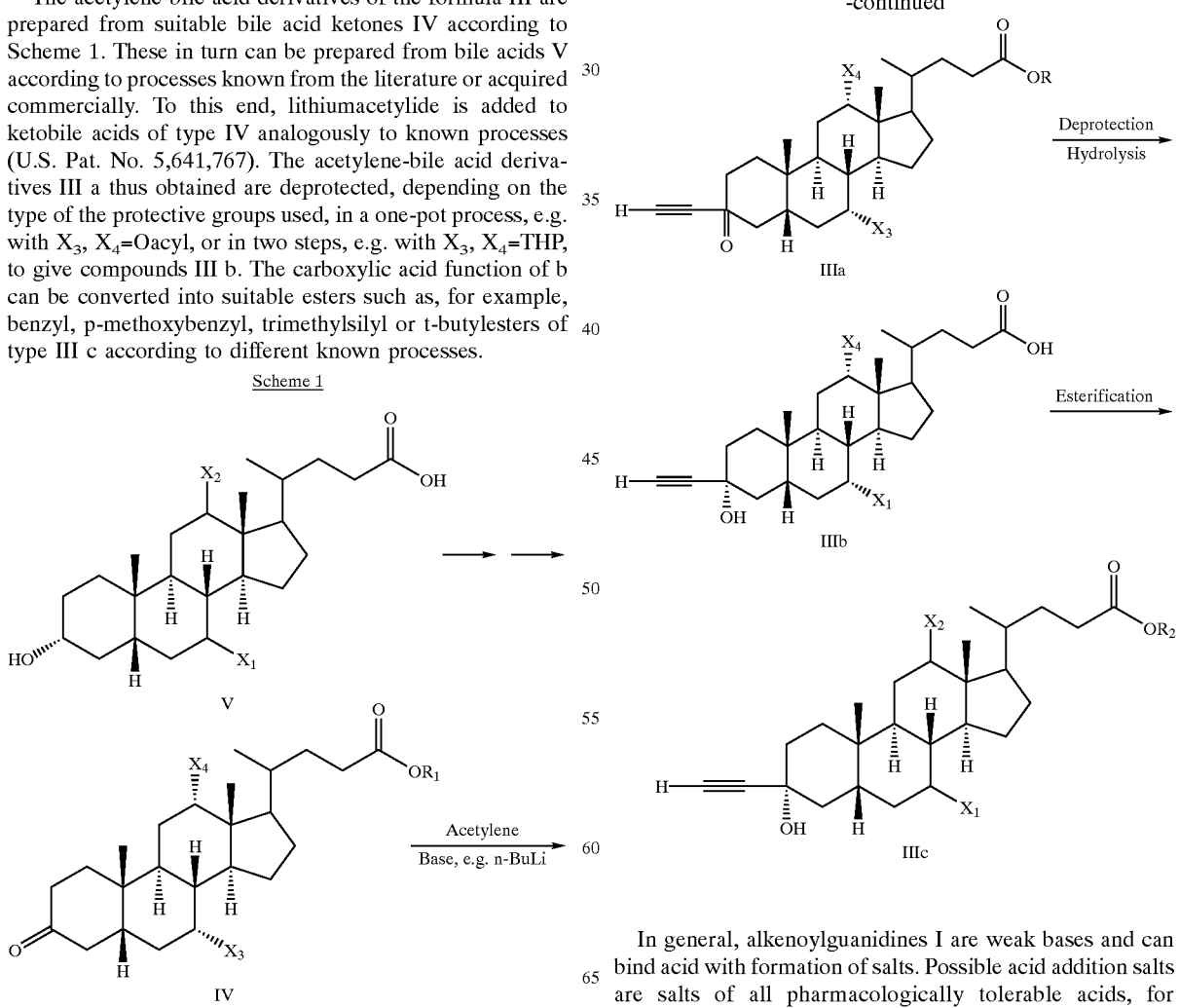

In general, alkenoylguanidines I are weak bases and can bind acid with formation of salts. Possible acid addition salts are salts of all pharmacologically tolerable acids, for example halides, in particular hydrochlorides, lactates, sulfates, citrates, tartrates, acetates, phosphates, methylsulfonates, p-toluenesulfonates.

The compounds of the formula I are substituted acylguanidines.

The compounds of the formula (I) according to the invention also pass into the hepatobiliary system and therefore act in these tissues. Thus, for example, the absorption of water from the gall bladder is inhibited by inhibition of the apical NHE antiport of subtype 3 of the gall bladder epithelium, which results in dilute bile fluid.

The term "physiologically functional derivative" used here designates that physiologically tolerable derivative of a compound of the formula I according to the invention, e.g. an ester, which on administration to a mammal, such as, for example, man, is able (directly or indirectly) to form a compound of the formula I or an active metabolite thereof.

The physiologically functional derivatives also include prodrugs of the compounds according to the invention. Such prodrugs can be metabolized in vivo to a compound according to the invention. These prodrugs themselves can be active or inactive.

The compounds according to the invention can also be present in various polymorphic forms, e.g. as amorphous and crystalline polymorphic forms. All polymorphic forms of the compounds according to the invention are included in the scope of the invention and are a further aspect of the invention.

Below, all references to "compound(s) according to formula (I)" relate to compound(s) of the formula (I) as described above, and its/their salts, solvates and physiologically functional derivatives as described herein.

The amount of a compound according to formula (I) which is necessary in order to achieve the desired biological effect is dependent on a number of factors, e.g. on the selected specific compound, the intended use, the manner of administration and the clinical condition of the patient.

In general, the daily dose is in the range from 0.1 mg to 100 mg (typically from 0.1 mg to 50 mg) per day per kilogram of bodyweight, e.g. 0.1–10 mg/kg/day. Tablets or capsules can contain, for example, from 0.01 to 100 mg, typically from 0.02 to 50 mg. In the case of pharmaceutically tolerable salts, the abovementioned weight details relate to the weight of the aminopropanol ion derived from the salt. For the prophylaxis or therapy of the abovementioned conditions, the compounds according to formula (I) themselves can be used as the compound, but they are preferably present with a tolerable carrier in the form of a pharmaceutical composition. The carrier must of course be tolerable, in the sense that it is compatible with the other constituents of the composition and is not harmful to the health of the patient. The carrier can be a solid or a liquid or both and is preferably formulated with the compound as an individual dose, for example as a tablet, which can contain from 0.05% to 95% by weight of the active compound. Further pharmaceutically active substances can also be present, including further compounds according to formula (I), and including one or more hypolipidemic active compounds. The pharmaceutical compositions according to the invention can be prepared according to one of the known pharmaceutical methods, which essentially consist in mixing the constituents with pharmacologically tolerable vehicles and/or excipients.

Pharmaceutical compositions according to the invention are those which are suitable for oral and peroral (e.g. sublingual) administration, although the most suitable manner of administration in each individual case is dependent on the nature and severity of the condition to be treated and on the type of the compound according to formula (I) used in each case. Sugar-coated formulations and sugar-coated delayed release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets which in each case contain a certain amount of the compound according to formula (I); as powders or granules; as a solution or suspension in an aqueous or nonaqueous liquid; or as an oil-in-water or water-in-oil emulsion. As already mentioned, these compositions can be prepared according to any suitable pharmaceutical method which includes a step in which the active compound and the carrier (which can consist of one or more additional constituents) are brought into contact. In general, the compositions are produced by uniform and homogeneous mixing of the active compound with a liquid and/or finely divided solid carrier, after which the product, if necessary, is shaped. Thus, for example, a tablet can be prepared by compressing or shaping a powder or granules of the compound, if appropriate with one or more additional constituents. Pressed tablets can be prepared by tableting the compound in free-flowing form, such as, for example, a powder or granules, if appropriate mixed with a binder, lubricant, inert diluent and/or one (a number of) surface-active/dispersing agents in a suitable machine. Shaped tablets can be prepared by shaping the powdered compound moistened with an inert liquid diluent in a suitable machine.

Pharmaceutical compositions which are suitable for peroral (sublingual) administration include lozenges which contain a compound according to formula (I) with a flavoring, customarily sucrose and gum arabic or tragacanth, and pastilles which comprise the compound in an inert base such as gelatin and glycerol or sucrose and gum arabic.

Experimental Section

List of abbreviations:

| | |
|---|---|
| $CH_2Cl_2$ | dichloromethane |
| DCC | dicyclohexylcarbodiimide |
| DCI | desorption chemical ionization |
| DIP | di-i-propyl ether |
| DME | dimethoxyethane |
| DMF | N,N-dimethylformamide |
| EA | ethyl acetate (EtOAc) |
| EI | electron impact |
| eq. | equivalent |
| ES | electron spray |
| FAB | fast atom bombardment |
| HEP | n-heptane |
| HOBT | benzotriazol-1-ol |
| KOtBu | potassium 2-methylpropan-2-olate |
| MeOH | methanol |
| m.p. | melting point |
| MTB | t-butyl methyl ether |
| RT | room temperature |
| THF | tetrahydrofuran |
| TOTU | O[(cyano(ethoxycarbonyl)methylene)amino]-1,1,3,3-tetramethyluronium tetrafluoroborate |

EXAMPLE 1

4-{3-[2-(2-{4-[2,6-Difluoro-4-(3-guanidino-2-methyl-3-oxopropenyl)phenoxy]phenyl}acetylamino)ethoxy]-7,12-dihydroxy-10,13-dimethylhexadecahydro-cyclopenta[a]phenanthren-17-yl}pentanoic acid

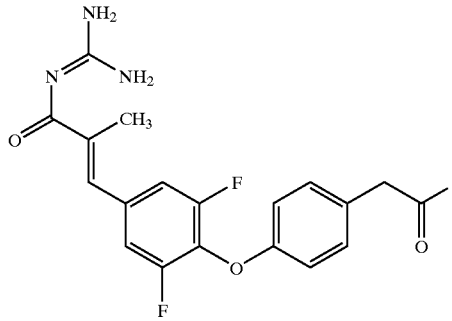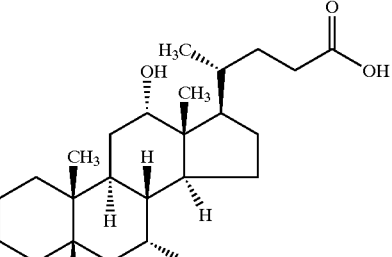

a) 4-(7,12-Dihydroxy-3-methanesulfonyloxy-10,13-dimethylhexadecahydrocyclopenta[a]phenanthren-17-yl)pentanoic acid 100 g of cholic acid are dissolved in 500 ml of pyridine and 23.1 ml of mesyl chloride are added dropwise over a period of 30 minutes at 0° C. The mixture is stirred at RT for 3 hours, then poured into a solution of 400 ml of $H_2SO_4$ in 3 l of water at 0° C. and extracted 4 times using 750 ml of EA each time. The extract is dried over $Na_2SO_4$ and the solvent is removed in vacuo. The residue is crystallized using diisopropyl ether and 117.1 g are obtained; m.p. 121° C. (with decomposition).

$R_f$(EA/HEP/acetic acid 5:5:1) = 0.31    MS (FAB) : 487 (M + H)$^+$ b) Methyl 4-[7,12-dihydroxy-3-(2-hydroxyethoxy)-10,13-dimethylhexadecahydrocyclopenta[a]phenanthren-17-yl] pentanoate 116 g of 4-(7,12-dihydroxy-3-methanesulfonyloxy-10,13-dimethylhexadecahydrocyclopenta[a]phenanthren-17-yl) pentanoic acid and 130 ml of triethylamine are dissolved in 650 ml of glycol and stirred at 100° C. for 3 hours and 115° C. for 7.5 hours. The reaction mixture is poured into a solution of 400 ml of $H_2SO_4$ in 3 l of water at 0° C. and extracted 7 times using 750 ml of EA each time. The extract is dried over $Na_2SO_4$ and the solvent is removed in vacuo. The intermediate product IP is obtained. 130 ml of acetyl chloride are added dropwise to 900 ml of methanol at 0° C. A solution of IP in 400 ml is then added and the mixture is stirred at RT for 6 hours. It is allowed to stand at RT for 60 hours, then poured into 2.6 l of water and extracted 8 times using 500 ml of diisopropyl ether (DIP) each time. The organic phase is then washed a further 6 times with 600 ml of a semisaturated aqueous $NaHCO_3$ solution each time. It is dried over $Na_2SO_4$ and the solvent is removed in vacuo. Chromatography on silica gel using EA yields 32 g of a resinous solid.

$R_f$(EA) = 0.19    MS (FAB) : 467 (M + H)$^+$ c) Methyl 4-{3-[2-(1,3-dioxo-1,3-dihydroisoindol-2-yl)ethoxy]-7,12-dihydroxy-10,13-dimethylhexadecahydrocyclopenta[a]phenanthren-17-yl}pentanoate 1.5 g of methyl 4-[7,12-Dihydroxy-3-(2-hydroxyethoxy)-10,13-dimethylhexadecahydrocyclopenta[a]phenanthren-17-yl]pentanoate, 950 mg of triphenylphosphine and 550 mg of phthalimide are warmed to 45° C. in 26 ml of THF and 1.14 ml of diethyl azodicarboxylates are added dropwise at this temperature. The reaction mixture is stirred at 45° C. for 2 hours, then poured into 200 ml of a semiconcentrated aqueous $NaHCO_3$ solution and extracted 3 times using 200 ml of EA each time. The extract is dried over $Na_2SO_4$ and the solvent is removed in vacuo. Chromatography on silica gel using t-butyl methyl ether (MTB) yields 1.76 g of a viscous oil $R_f$(EA) = 0.60    MS (FAB) : 602 (M + Li)$^+$ d) Methyl 4-[3-(2-aminoethoxy)-7,12-dihydroxy-10,13-dimethylhexadecahydrocyclopenta[a]phenanthren-17-yl] pentanoate 1.7 g of methyl 4-{3-[2-(1,3-dioxo-1,3-dihydroisoindol-2-yl)ethoxy]-7,12-dihydroxy-10,13-dimethylhexadecahydrocyclopenta[a]phenanthren-17-yl}pentanoate and 0.52 ml of hydrazine hydrate (80%) are dissolved in 14 ml of methanol and the solution is refluxed for 3 hours. It is then cooled to 40° C. and the reaction mixture is treated with 8.7 ml of a 2N aqueous HCl solution. It is stirred at 40° C. for 30 minutes, then the volatile constituents are removed in vacuo. Chromatography on silica gel using acetone/water 10:1 yields 540 mg of resinous solid.

$R_f$(acetone/water 10:1) = 0.06    MS (FAB) : 466 (M + H)$^+$ e) Methyl 4-(7,12-dihydroxy-3-{2-[2-(4-hydroxyphenyl)acetylamino]ethoxy}-10,13-dimethylhexadecahydrocyclopenta[a]phenanthren-17-yl) pentanoate 700 mg of methyl 4-[3-(2-aminoethoxy)-7,12-dihydroxy-10,13-dimethylhexadecahydrocyclopenta[a]phenanthren-17-yl]pentanoate, 230 mg of 4-hydroxyphenylacetic acid and 305 mg of HOBT are dissolved in 10 ml of THF and a solution of 342 mg of DCC in 10 ml of THF is injected at 0° C. The mixture is stirred at 0° C. for one hour and then at RT for 25 hours. The precipitate is filtered off, the filtrate is diluted with 150 ml of a 10% aqueous $NaHCO_3$ solution and the mixture is extracted three times with 100 ml of EA each time. The extract is dried over $Na_2SO_4$ and the solvent is removed in vacuo. Chromatography on silica gel using EA/MeOH 10:1 yields 660 mg of a colorless oil.

$R_f$(EA/MeOH 10:1) = 0.38    MS (FAB) : 600 (M + H)$^+$ f) 4-(7,12-Dihydroxy-3-{2-[2-(4-hydroxyphenyl)acetylamino]ethoxy}-10,13-dimethylhexadecahydrocyclopenta[a]phenanthren-17-yl)pentanoic acid 620 mg of 4-(7,12-dihydroxy-3-{2-[2-(4-hydroxyphenyl)acetylamino]ethoxy}-10,13-dimethylhexadecahydrocyclopenta[a]phenanthren-17-yl)pentanoic acid are dissolved in 10 ml of MeOH and 3.1 ml of a 1N aqueous NaOH solution are added at RT. The mixture is stirred at RT for 25 hours, treated with 150 ml of a 2N aqueous HCl solution and extracted 3 times using 100 ml of EA each time. The extract is dried over $Na_2SO_4$ and the solvent is removed in vacuo. 630 mg of a product contaminated with small amounts of acetic acid are obtained, which are reacted without further purification.

$R_f$(EA/MeOH 5:1) = 0.30    MS (ES) : 586 (M + H)$^+$ g) Ethyl 2-methyl-3-(3,4,5-trifluorophenyl)acrylate 4.3 ml of triethyl 2-phosphonopropionate are dissolved in 30 ml of anhydrous THF and 12.5 ml of a 1.6 N solution of n-butyllithium in hexane are added dropwise at 0° C. The mixture is stirred at RT for 15 minutes and a solution of 3.2 g of 3,4,5-trifluorobenzaldehyde in 8 ml of anhydrous THF is then added dropwise. It is stirred at RT for one hour and allowed to stand at RT for 16 hours. The reaction mixture is diluted with 300 ml of water, 30 ml of a saturated aqueous $Na_2CO_3$ solution are added and it is extracted 3 times using 100 ml of EA each time. The extract is dried over $Na_2SO_4$ and the solvent is removed in vacuo. Chromatography on silica gel using EA/HEP 1:8 yields 3.8 g if colorless crystals; m.p. 54° C.

$R_f$(EA/HEP 1:8) = 0.35    MS (DCl) : 245 (M + H)$^+$ h) Ethyl 3-{4-[4-({2-[17-(3-Carboxy-1-methylpropyl)-7,12-dihydroxy-10,13-dimethylhexadecahydrocyclopenta[a]phenanthren-3-yloxy]ethylcarbamoyl}methyl)phenoxy]-3,5-difluorophenyl}-2-methylacrylate 610 mg of 4-(7,12-dihydroxy-3-{2-[2-(4-hydroxyphenyl)acetylamino]ethoxy}-10,13-dimethylhexadecahydrocyclopenta[a]phenanthren-17-yl)pentanoic acid, 232 mg of ethyl 2-methyl-3-(3,4,5-trifluorophenyl)acrylate and 393 mg of $K_2CO_3$ are suspended in 5 ml of DMF (anhydrous) and the suspension is stirred at 150° C. for 160 minutes. After cooling, the reaction mixture is taken up using 150 ml of a 2N aqueous HCl solution and extracted three times using 100 ml of EA each time. The extract is dried over $Na_2SO_4$ and the solvent is removed in vacuo. Chromatography on silica gel using EA/MeOH 10:1 yields 480 mg of resinous product.

$R_f$(EA/MeOH 10:1) = 0.27    MS (ES) : 810 (M + H)$^+$ i) 4-{3-[2-(2-{4-[2,6-difluoro4-(3-guanidino-2-methyl-3-oxopropenyl)phenoxy]phenyl}acetylamino)ethoxy]-7,12-dihydroxy-10,13-dimethylhexadecahydrocyclopenta[a]phenanthren-17-yl}pentanoic acid 311 mg of guanidine hydrochloride are dissolved in 3 ml of DMF (anhydrous) and a solution of 332 mg of KOtBu in 3 ml of DMF (anhydrous) is added at RT. The mixture is stirred at RT for one hour, then a solution of 480 mg of ethyl 3-{4-[4-({2-[17-(3-carboxy-1-methylpropyl)-7,12-dihydroxy-10,13-dimethylhexadecahydrocyclopenta[a]phenanthren-3-yloxy]ethyl-carbamoyl}methyl)phenoxy]-3,5-difluorophenyl}-2-methylacrylate in 3 ml of DMF (anhydrous) is added. The reaction mixture is stirred at RT for 65 hours and then diluted with 200 ml of water. It is adjusted to pH=7 using 4N aqueous HCl solution and extracted three times using 150 ml of EA each time. The extract is dried over $Na_2SO_4$ and the solvent is removed in vacuo. Chromatography on silica gel using $CH_2C_2$/MeOH/acetone/water/acetic acid 64:8:8:1:1yields 230 mg of an amorphous solid.

Rf($CH_2Cl_2$/MeOH/acetone/water/acetic acid 64:8:8:1:1)= 0.27

MS (ES): 823 (M+H)$^+$

The compound of Example 2 was prepared analogously to Example 1 from 4-(3-amino-7,12-dihydroxy-10,13-dimethylhexadecahydrocyclopenta[a]phenanthren-17-yl)-pentanoic acid:

EXAMPLE 2

4-[3-(2-{4-[2,6-Difluoro-4-(3-guanidino-1-methyl-3-oxopropenyl)phenoxy]phenyl}acetylamino)-7,12-dihydroxy-10,13-dimethylhexadecahydrocyclopenta[a]phenanthren-17-yl]pentanoic acid

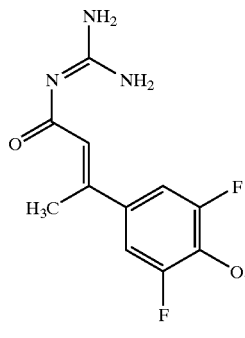
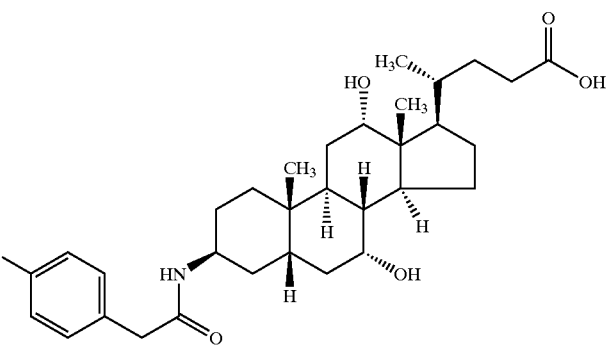

m.p. 190° C. (with decomposition)
Rf(CH₂Cl₂/MeOH/water/acetic acid 32:8:1:1)=0.36
MS (ES): 779 (M+H)⁺

EXAMPLE 3

4-(3-{2-[(4'-Guanidinocarbonylbiphenyl-3-carbonyl)
amino]ethoxy}-7,12-dihydroxy-10,13-
dimethylhexadecahydrocyclopenta[a]phenanthren-
17-yl)pentanoic acid

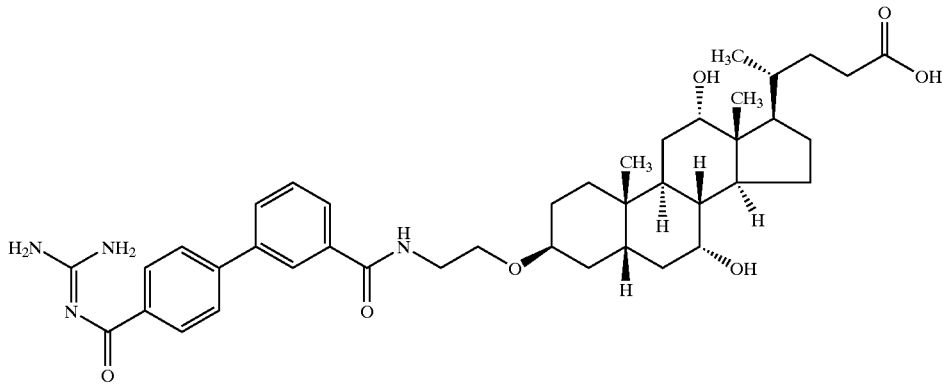

a) Methyl 4-{3-[2-(3-bromobenzoylamino)ethoxy]-7,12-
dihydroxy-10,13-dimethylhexadecahydrocyclopenta[a]
phenanthren-17-yl}pentanoate 932 mg of methyl 4-[3-(2-aminoethoxy)-7,12-dihydroxy-10,13-dimethylhexadecahydrocyclopenta[a]phenanthren-17-yl]pentanoate (Example 1d) and 402 mg of 3-bromobenzoic acid are dissolved in 20 ml of anhydrous DMF and first 656 mg of O[(cyano(ethoxycarbonyl)methylene)amino]-1,1,3,3-tetramethyluronium tetrafluoroborate (TOTU) (Proceedings of the 21st European Peptide Symposium, Peptides 1990, Editors E. Giralt and D. Andreu, Escom, Leiden, 1991) and then 760 μL of N-ethylmorpholine are added at 0° C. The reaction mixture is stirred at RT for 20.5 hours and then poured into 100 ml of a 10% aqueous NaHCO₃ solution. It is extracted 3 times using 150 ml of EA each time. The extract is dried over Na₂SO₄ and the solvent is removed in vacuo. Chromatography on silica gel using EA yields 610 mg of a viscous oil.

| R_f(EA) = 0.33 | MS (ES) : 649 (M + H)⁺ |
|---|---| b) 4-{3-[2-(3-Bromobenzoylamino)ethoxy]-7,12-
dihydroxy-10,13-dimethylhexadecahydrocyclopenta[a]
phenanthren-17-yl}pentanoic acid 600 mg of methyl 4-{3-[2-(3-bromobenzoylamino)ethoxy]-7,12-dihydroxy-10,13-dimethylhexadecahydrocyclopenta[a]phenanthren-17-yl}pentanoate are dissolved in 19 ml of methanol and 4.6 ml of a 1N aqueous NaOH solution are added. The mixture is stirred at RT for 6 hours, then poured into 150 ml of a 2N aqueous HCl solution and extracted 4 times using 150 ml of MTB each time. The extract is dried over Na₂SO₄ and the solvent is removed in vacuo. 550 mg of a viscous oil are obtained, which are employed further as such.

| R_f(EA/MeOH 5:1) = 0.46 | MS (ES) : 635 (M + H)⁺ |
|---|---| c) Ethyl 3'-{2-[17-(3-carboxy-1-methylpropyl)-7,12-
dihydroxy-10,13-dimethylhexadecahydrocyclopenta[a]
phenanthren-3-yloxy]ethylcarbamoyl}biphenyl-4-
carboxylate.

540 mg of 4-{3-[2-(3-bromobenzoylamino)ethoxy]-7,12-dihydroxy-10,13-dimethylhexadecahydrocyclopenta[a]phenanthren-17-yl}pentanoic acid, ethyl 4-hydroxyborylbenzoate, 9.6 mg of Pd(II) acetate and 22.3 mg of triphenylphosphine are dissolved in 5.1 ml of toluene and 1.4 ml of ethanol and 425 μL of a 2N aqueous Na₂CO₃ solution are added. The mixture is refluxed for 3 hours, and a further 33.8 mg of ethyl 4-dihydroxyborylbenzoate and 425 μL of a 2N aqueous Na₂CO₃ solution are then added and the mixture is refluxed again for 1 hour 35 minutes. 33.8 mg of ethyl 4-dihydroxyborylbenzoate and 425 μL of a 2N aqueous Na₂CO₃ solution are then again added and the mixture is additionally refluxed for 4 hours 40 minutes. After cooling, the reaction mixture is taken up using 150 ml of a 2N aqueous HCl solution and extracted 4 times using 100 ml of EA each time. The extract is dried over Na₂SO₄ and the solvent is removed in vacuo. Chromatography on silica gel using MTB/2% acetic acid yields 510 mg of a colorless foam.

| R_f(MTB/2% acetic acid) = 0.21 | MS (ES) : 635 (M + H)⁺ |
|---|---| d) 4-(3-{2-[(4'-Guanidinocarbonylbiphenyl-3-carbonyl)
amino]ethoxy}-7,12-dihydroxy-10,13-
dimethylhexadecahydrocyclopenta[a]phenanthren-17-yl)
pentanoic acid 115 mg of guanidine hydrochloride are dissolved in 2 ml of anhydrous DMF and a solution of 122 mg of potassium t-butoxide in 2 ml of anhydrous DMF are added at RT. The mixture is stirred at RT for one hour and a solution of 150 mg of ethyl 3'-{2-[17-(3-carboxy-1-methylpropyl)-7,12-dihydroxy-10,13-dimethylhexadecahydrocyclopenta[a]phenanthren-3-yloxy]ethylcarbamoyl}biphenyl-4-carboxylate in 3 ml of anhydrous DMF is then added. The reaction mixture is stirred at RT for 4 days and 2 hours, then it is treated with 35 ml of water and adjusted to pH=6.5 using aqueous HCl solution. It is stirred for 1 hour and the main part of the product is precipitated. The filtrate is extracted 3 times using 100 ml of EA each time. The extract is dried over $Na_2SO_4$ and the solvent is removed in vacuo. Chromatography on silica gel using $CH_2Cl_2$/MeOH/acetone/water/acetic acid 64:8:8:1:1 yields 60 mg of an amorphous solid.

Rf($CH_2Cl_2$/MeOH/acetone/water/acetic acid 64:8:8:1:1)= 0.13

MS (ES): 635 $(M+H)^+$

The absorption of water from the gall bladder is inhibited by inhibition of the apical NHE antiport of the subtype 3 of the gall bladder epithelium, which results in a dilute bile fluid. This dilute bile fluid prevents gallstone formation and, if gallstones are already present, brings about their dissolution. The inhibition of the NHE antiport of the subtype 3 by the compounds of the formula I according to the invention was determined by means of the following test.

Most of the molecular bilology techniques follow protocols from the works "Current Protocols in Molecular Biology (eds. Ausubel, F. M., Brent, R., Kingston, R. E., Moore, D. D., Seidman, J. G., Smith, J. A. and Struhl, K.; John Wiley & Sons)" and "Molecular Cloning: A Laboratory Manual (Sambrock, J., Fritsch, E. F. und Maniatis, T.; Cold Spring Harbor Laboratory Press (1989))". In the context of our studies, stably transfected cell lines were produced which in each case express one of the following NHE subtypes: human NHE1 (Sardet et al.; Cell 56, 271–280 (1989), rabbit NHE2 (Tse et al.; J. Biol. Chem. 268, 11917–11924 (1993)) or rat NHE3 (Orlowski et al.; J. Biol. Chem. 267, 9331–9339 (1992)), human NHE3 (Braut et al.; Am. J. Physiol. 269, 198–206 (1995)). The cDNA clones of the respective NHE subtypes obtained by Prof. Pouysségur were cloned into the expression plasmid pMAMneo (obtainable, for example, through CLONTECH, Heidelberg) after addition of suitable linker sequences such that the NHE1 recognition sequence of the plasmid is approximately 20–100 base pairs before the start codon of the respective NHE subtype and the entire coding sequence is present in the construct. Using the so-called "calcium phosphaste method" (described in chapter 9.1 of "Current Protocols in Molecular Biology"), the NHE-defined cell line LAP1 (Franchi et al.; Proc. Natl. Acad. Sci. USA 83, 9388–9392 (1986)) was transfected with the plasmids which contain the respective coding sequences of the NHE-subtypes. After selection for transfected cells by means of growth in G418-containing medium (only cells which have received a neo-gene by transfection can survive under these conditions), selection for functional NHE expression was carried out. For this, the "acid load" technique described by Sardet was used (Sardet et al.; Cell 56, 271–280 (1989)). Cells which express a functional NHE subtype can also compensate for the acidification carried out in this test in the absence of $CO_2$ and $HCO_3$—, but not untransfected LAP1 cells. After repetition of the "acid load" selection several times, the surviving cells were inoculated into microtiter plates such that statistically one cell per well should occur. After approximately 10 days, how many colonies grew per well was checked under the microscope. Cell populations of individual colonies were then investigated using the XTT proliferation kit (Boehringer Mannheim) with respect to their ability to survive after "acid load". The best cell lines were used for the further tests and, to avoid a loss of transfected sequence, cultured in G418-containing medium under continuous selection pressure. For the determination of $IC_{50}$ values for the inhibition of the individual NHE subtypes by specific substances, a test developed by S. Faber (Faber et al.; Cell. Physiol. Biochem. 6, 39–49 (1996)), which is based on the "acid load" technique, was slightly modified. In this test, the increase in the intracellular pH (pHi) after an acidification was determined which commenced with functional NHE even under bicarbonate-free conditions. For this, the pHi was determined using the pH-sensitive fluorescent dye BCECF (Calbiochem, the precursor BCECF-AM is employed). The cells were first loaded with BCECF. The BCECF fluorescence was determined in a "ratio fluorescence spectrometer" (Photon Technology International, South Brunswick, N.J., USA) at excitation wavelengths of 505 and 440 nm and an emission wavelength of 535 nm and converted into the pHi by means of calibration curves. Deviating from the protocol described, the cells were incubated in $NH_4Cl$ buffer (pH 7.4) even during BCECF loading ($NH_4Cl$ buffer: 115 mM NaCl, 20 mM $NH_4Cl$, 5 mM KCl, 1 mM $CaCl_2$, 1 mM $MgSO_4$, 20 mM hepes, 5 mM glucose, 1 mg/ml of BSA; a pH of 7.4 is set using 1 M NaOH). The intracellular acidification was induced by addition of 975 µl of an $NH_4Cl$-free buffer to 25 µl aliquots of the cells incubated in $NH_4Cl$ buffer. The subsequent rate of the pH recovery was recorded for 2 minutes in the case of NHE1, 5 minutes in the case of NHE2 and 3 minutes in the case of NHE3. For the calculation of the inhibitory potency of the tested substances, the cells were first investigated in buffers in which a complete or no pH recovery at all took place. For complete pH recovery (100%), the cells were incubated in $Na^+$-containing buffer (133.8 mM NaCl, 4.7 mM KCl, 1.25 mM $CaCl_2$, 1.25 mM $MgCl_2$, 0.97 mM $Na_2HPO_4$, 0.23 mM $NaH_2PO_4$, 5 mM hepes, 5 mM glucose, a pH of 7.0 is set using 1 M NaOH). For the determination of the 0% value, the cells were incubated in an $Na^+$-free buffer (133.8 mM choline chloride, 4.7 mM KCl, 1.25 mM $CaCl_2$, 1.25 mM $MgCl_2$, 0.97 mM $K_2HPO_2$, 0.23 mM $KH_2PO_4$, 5 mM hepes, 5 mM glucose, a pH of 7.0 is set using 1 M NaOH). The substances to be tested were prepared in the $Na^+$-containing buffer. The recovery of the intracellular pH at each tested concentration of the substance was expressed in % of the maximum recovery. The $IC_{50}$ value of the respective substance was calculated for the individual NHE subtypes from the percentage values of the pH recovery by means of the SigmaPlot program.

Results of the inhibition of the human $Na^+/H^+$ exchanger (subtype 3; NHE-3):

| Example (see exp. section) | Residual activity at 30 µM |
| --- | --- |
| 1 | 17% |
| 2 | 10% |
| 3 | 65% |

From the measured data, it is evident that the compounds of the formula I according to the invention inhibit the NHE antiport up to 65%.

We claim:

1. A compound of the formula I

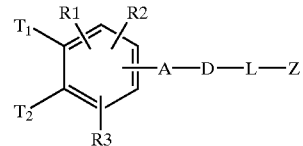

in which:

T1 and T2 independently of one another are

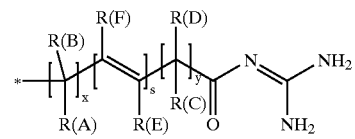

or hydrogen, where

T1 and T2 cannot simultaneously be hydrogen;

Z is

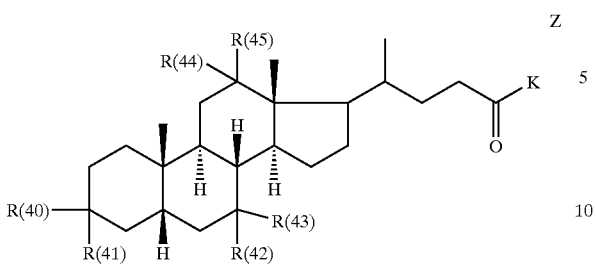

A is a bond, $(C_1-C_4)$-alkyl, or $(C_0-C_4)$-alkyl-X;

X is —O—, —CO—, —CH[OH]—, —CH[OCH$_3$]—, —SO$_{(0-2)}$—, —NH—, or —N(CH$_3$)—;

D is phenylene which is not substituted or is substituted by 1–3 substituents selected from the group consisting of F, Cl, —CF$_3$, $(C_1-C_4)$-alkyl, hydroxyl, methoxy, —NH$_2$, NHCH$_3$, N(CH$_3$)$_2$, CH$_3$SO$_2$— and H$_2$NO$_2$S—;

R(A), R(B), R(C), R(D), R(E), R(F) independently of one another are hydrogen, F, Cl, Br, I, CN, OH, OR(6), NR(7)R(8), $(C_1-C_8)$-alkyl, O—$(C_1-C_{12})$-alkyl, or $(C_3-C_8)$-cycloalkyl, it being possible in the alkyl radicals for one, a number or all hydrogens to be replaced by fluorine;

R(6) is $(C_3-C_6)$-alkenyl, $(C_3-C_8)$-cycloalkyl, phenyl or benzyl, it being possible for the phenyl nucleus to be up to trisubstituted by F, Cl, CF$_3$, methyl, methoxy, and/or NR(9)R(10);

R(9), R(10) independently of one another are H, $(C_1-C_4)$-alkyl or $(C_1-C_4)$-perfluoroalkyl;

R(7) and R(8) independently of one another are $(C_1-C_4)$-alkyl, $(C_3-C_6)$-alkenyl, $(C_3-C_8)$-cycloalkyl, phenyl or benzyl, it being possible for the phenyl nucleus to be up to trisubstituted by F, Cl, CF$_3$, methyl, methoxy, and/or NR(9)R(10); or R(7) and R(8) together form a chain of 4 or 5 methylene groups, of which one CH$_2$ group can be replaced by oxygen, sulfur, NH, N—CH$_3$ or N-benzyl;

s is zero or 1, x is zero, 1 or 2;

y is zero, 1 or 2;

R(1), R(2), R(3) independently of one another are hydrogen, F, Cl, Br, I, CN, —(C=O)—N=C(NH$_2$)$_2$, —SO$_{(0-1)}$—$(C_1-C_8)$-alkyl, O—$(C_0-C_4)$-alkylphenyl, —$(C_0-C_4)$-alkylphenyl, it being possible for the phenyl nucleus to be up to trisubstituted by F, Cl, CF$_3$, methyl, methoxy, and/or —$(C_0-C_4)$-alkyl-NR(21)R(22); $(C_1-C_8)$-alkyl, O—$(C_1-C_{12})$-alkyl, or $(C_3-C_8)$-cycloalkyl, it being possible in the alkyl radicals for one, a number or all hydrogens to be replaced by fluorine;

R(21), R(22) independently of one another are H or $(C_1-C_4)$-alkyl;

L is $(C_1-C_{15})$-alkyl, it being possible for one or more (CH$_2$) groups to be replaced by —CH=CH—, —C≡C—, —O—, —NR(47)-, —NR(48)-, —CO—, and/or —SO$_2$—;

R(47) is hydrogen, $(C_1-C_8)$-alkyl, R(48)-CO—, phenyl, or benzyl;

R(48) is hydrogen, $(C_1-C_8)$-alkyl, phenyl, or (CH$_2$)-phenyl, it being possible for the phenyl nucleus to be up to trisubstituted by F, Cl, CF$_3$, methyl, and/or methoxy;

R(40) to R(45) independently of one another are H, —O R(50), —S R(50), NH R(50), —N R(50)$_2$, —O—(CO)— R(50), —S—(CO)— R(50), —NH—(CO)— R(50), —O—PO—(O R(50))-O R(50), —O—(SO$_2$)—O R(50), —R(50), a bond to L; or R(40) and R(41), R(42) and R(43), R(44) and R(45) in each case together are the oxygen of a carbonyl group;

just one of the radicals always having the meaning of a bond to L;

R(50) is hydrogen, $(C_1-C_4)$-alkyl, phenyl, or (CH$_2$)-phenyl, it being possible for the phenyl nucleus to be up to trisubstituted by F, Cl, CF$_3$, methyl, and/or methoxy;

K is —OR(51), —NH(R51), —N(R51)$_2$, —HN—CH$_2$—CH$_2$—CO$_2$H, —HN—CH$_2$—CH$_2$—SO$_3$H, —N(CH$_3$)CH$_2$CO$_2$H, —HN—CH(R46)CO$_2$H, or —OKa, Ka being a cation;

R(46) is hydrogen, C$_1$-C$_4$-alkyl, benzyl, —CH$_2$—OH, H$_3$CSCH$_2$CH$_2$—, HO$_2$CCH$_2$—, or HO$_2$CCH$_2$CH$_2$—;

R(51) is H, $(C_1-C_4)$-alkyl, phenyl, or (CH$_2$)-phenyl, it being possible for the phenyl radical to be up to trisubstituted by F, Cl, CF$_3$, methyl, and/or methoxy;

or a pharmaceutically tolerable salt or physiologically functional derivative thereof.

2. A compound as claimed in claim 1, wherein

T1 and T2 independently of one another are

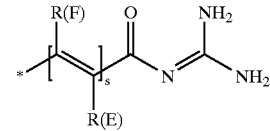

or hydrogen, where

T1 and T2 canot simultaneously be hydrogen

L—Z is

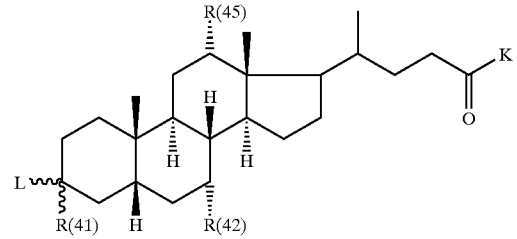

A is a bond, —CH$_2$—, or CH$_2$—X—;

X is —O—, —CO—, —CH[OH]—, —CH[OCH$_3$]—, —SO$_{(0-2)}$—, —NH—, or N(CH$_3$)—;

s is zero or 1;

D is phenylene which can be up to disubstituted by F, Cl, —CF$_3$, $(C_1-C_4)$-alkyl, hydroxyl, methoxy, —NH$_2$, NHCH$_3$, N(CH$_3$)$_2$, CH$_3$SO$_2$—, and/or H$_2$NO$_2$S—;

R(E) is F, Cl, CN, OR(12), $(C_1-C_4)$-alkyl, O—$(C_1-C_4)$-alkyl, or $(C_3-C_6)$-cycloalkyl, it being possible in the alkyl radicals for one, a number or all hydrogens to be replaced by fluorine;

R(6) is $(C_3-C_6)$-alkenyl, $(C_3-C_8)$-cycloalkyl, phenyl or benzyl, it being possible for the phenyl nucleus to be up to trisubstituted by F, Cl, CF$_3$, methyl, methoxy, and/or NR(9)R(10);

R(9), R(10) independently of one another are H, $(C_1-C_4)$-alkyl or $(C_1-C_4)$-perfluoroalkyl;

R(F) is hydrogen;

R(1), R(2), R(3) independently of one another are hydrogen, F, Cl, Br, I, CN, —(C=O)—N=C(NH$_2$)$_2$, —SO$_{(0-1)}$—$(C_1-C_8)$-alkyl, O—$(C_0-C_4)$-alkylphenyl, or —$(C_0-C_4)$-alkylphenyl, it being possible for the phenyl nucleus to be up to trisubstitued by F, Cl, CF$_3$, methyl, and/or methoxy;

L is $(C_1-C_8)$-alkyl, where one or more $(CH_2)$ groups can be replaced by —CH=CH—, —C≡C—, —O—, —NR(47)-, —NR(48)-, —CO—, and/or —SO$_2$—;

R(47) is hydrogen, $(C_1-C_4)$-alkyl, R(48)-CO—, phenyl, or $(CH_2)$-phenyl;

R(48) is hydrogen, $(C_1-C_4)$-alkyl, phenyl, or $(CH_2)$-phenyl, it being possible for the phenyl nucleus to be up to trisubstituted by F, Cl, CF$_3$, methyl, and/or methoxy;

R(41), R(42), R(45) independently of one another are H, —O R(50), —S R(50), NH R(50), —N R(50)$_2$, —O—(CO)— R(50), —S—(CO)— R(50), —NH—(CO)—R(50), —O—PO—(O R(50))-O R(50), —O—(SO$_2$)—O R(50), or —R(50);

R(50) is hydrogen, $(C_1-C_4)$-alkyl, phenyl, or $(CH_2)$-phenyl, it being possible for the phenyl nucleus to be up to trisubstituted by F, Cl, CF$_3$, methyl, and/or methoxy;

K is —OR(51), —NH(R51), —N(R51)$_2$, —HN—CH$_2$—CH$_2$—CO$_2$H, —HN—CH$_2$—CH$_2$—SO$_3$H, —N(CH$_3$)CH$_2$CO$_2$H, —HN—CH(R46)CO$_2$H, or —OKa;

R(46) is H, $C_1-C_4$-alkyl, benzyl, —CH$_2$—OH, H$_3$CSCH$_2$CH$_2$—, HO$_2$CCH$_2$—, or HO$_2$CCH$_2$CH$_2$—;

R(51) is H, $(C_1-C_4)$-alkyl, phenyl, or $(CH_2)$-phenyl, it being possible for the phenyl radical to be up to trisubstituted by F, Cl, CF$_3$, methyl, and/or methoxy.

3. A compound as claimed in claim 1, wherein
T1 and T2 independently of one another are equal to

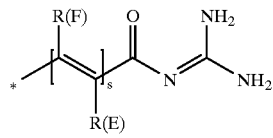

or hydrogen, where
T1 and T2 cannot simultaneously be hydrogen,
L—Z is

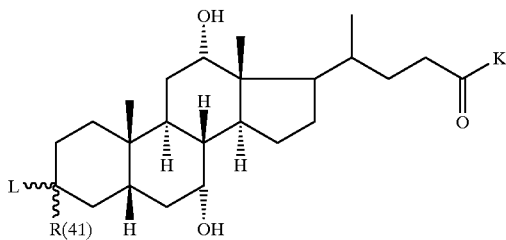

A is a bond, —CH$_2$—, CH$_2$—X—, or —X—;
X is —O—, —CO—, or —SO$_{(0-2)}$—;
s is zero or 1;
D is phenylene which can be up to disubstituted by F, Cl, —CF$_3$, $(C_1-C_4)$-alkyl, hydroxyl, methoxy, —NH$_2$, NHCH$_3$, N(CH$_3$)$_2$, CH$_3$SO$_2$—, and/or H$_2$NO$_2$S;

R(E) is F or $(C_1-C_4)$-alkyl, it being possible in the alkyl radical for one, a number or all hydrogens to be replaced by fluorine;

R(F) is hydrogen;

R(1), R(2), R(3) independently of one another are hydrogen, F, Cl, CN, —SO$_2$—CH$_3$, O—(C$_0$-C$_1$)-alkylphenyl, or —(C$_0$-C$_1$)-alkylphenyl, it being possible for the phenyl nucleus to be up to trisubstituted by F, Cl, CF$_3$, methyl, and/or methoxy;

L is $(C_1-C_8)$-alkyl, it being possible for one or more (CH$_2$) groups to be replaced by —CH=CH—, —C≡C—, —O—, —NR(47)-, —NR(48)-, —CO—, and/or —SO$_2$—;

R(47) is hydrogen, $(C_1-C_4)$-alkyl, R(48)-CO—, phenyl, or $(CH_2)$-phenyl;

R(48) is hydrogen, $(C_1-C_4)$-alkyl, phenyl or $(CH_2)$-phenyl, it being possible for the phenyl nucleus to be up to trisubstituted by F, Cl, CF$_3$, methyl, and/or methoxy;

R(41) is hydrogen or —OH;

K is —OR(51), —NH(R51), —N(R51)$_2$, —HN—CH$_2$—CO$_2$H, —HN—CH$_2$—CH$_2$—CO$_2$H, —HN—CH$_2$—CH$_2$—SO$_3$H, —N(CH$_3$)CH$_2$CO$_2$H, or —OKa;

R(51) is H, $(C_1-C_4)$-alkyl, phenyl, or $(CH_2)$-phenyl, it being possible for the phenyl radical to be up to trisubstituted by F, Cl, CF$_3$, methyl, and/or methoxy.

4. A compound as claimed in claim 1, wherein
T1 and T2 independently of one another are

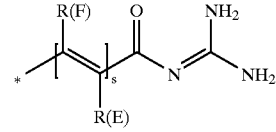

or hydrogen, where
T1 and T2 cannot simultaneously be hydrogen,
L—Z is

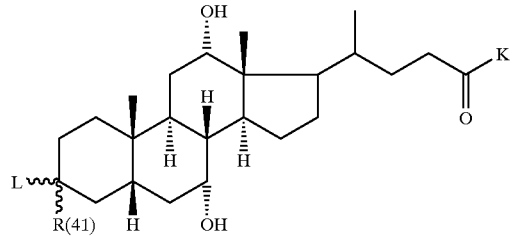

A is a bond or —O—;
s is zero or 1;
D is phenylene which can be up to disubstituted by F, Cl, —CF$_3$, $(C_1-C_4)$-alkyl, hydroxyl, methoxy, N(CH$_3$)$_2$, CH$_3$SO$_2$—, and/or H$_2$NO$_2$S;
R(E) is $(C_1-C_4)$-alkyl;
R(F) is hydrogen;
R(1), R(2), R(3) independently of one another are hydrogen, F, Cl, CN, —SO$_2$—CH$_3$, O—(C$_0$-C$_1$)-alkylphenyl, or —(C$_0$-C$_1$)-alkylphenyl, it being possible for the phenyl nucleus to be up to trisubstituted by F, Cl, CF$_3$, methyl, and/or methoxy;

L is $(C_1-C_6)$-alkyl, it being possible for one or more (CH$_2$) groups to be replaced by —CH=CH—, —C≡C—, —O—, —NR(47)-, —CO—, and/or —SO$_2$—;

R(47) is hydrogen or $(C_1-C_4)$-alkyl;
R(41) is hydrogen or —OH;
K is —OH, —HN—CH$_2$—CO$_2$H, —HN—CH$_2$—CH$_2$—CO$_2$H, —HN—CH$_2$—CH$_2$—SO$_3$H, —N(CH$_3$)CH$_2$CO$_2$H, or —OKa.

5. A compound as claimed in claim 1, wherein Ka is an alkali metal or alkaline earth metal ion or a quaternary ammonium ion.

6. A pharmaceutical composition, which comprises one or more compounds as claimed in claim 1 and a carrier.

7. A pharmaceutical composition as claimed in claim 6, which further comprises one or more hypolipidemic active compounds.

8. A method for the prophylaxis or treatment of gallstones, which comprises administering to a host in need of the prophylaxis or treatment an effective amount of a compound as claimed in claim 1.

9. A process for the preparation of a compound as claimed in claim 1, which comprises reacting, according to the following reaction scheme

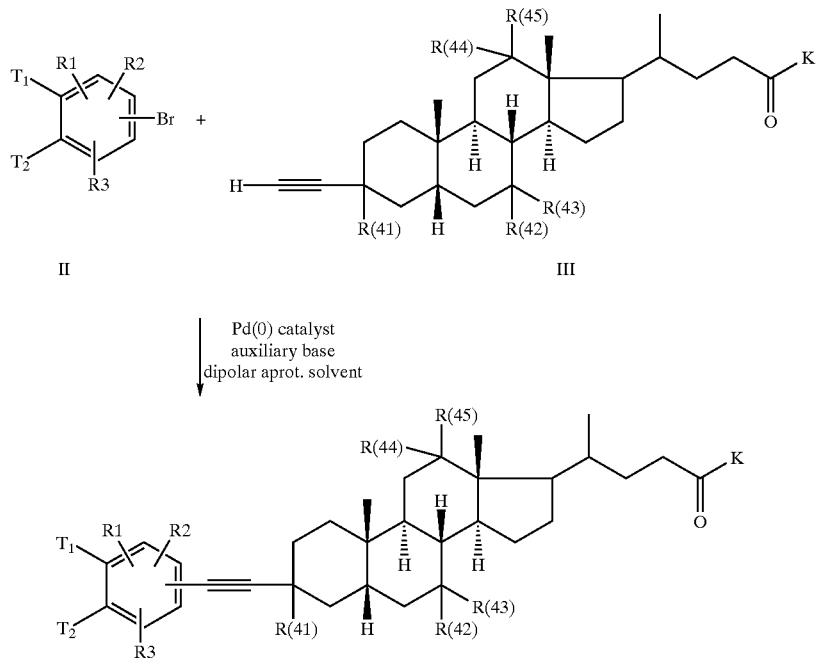
a compound of the formula II, in which T1, T2, R(1), R(2) and R(3) have the meanings indicated for formula I, with a compound L—Z of the formula III, in which R(41) to R(45) and K have the meanings indicated for formula I, to produce the compound as claimed in claim 1.
* * * * *